(12) United States Patent
Niemiec

(10) Patent No.: US 10,588,606 B2
(45) Date of Patent: Mar. 17, 2020

(54) ULTRASOUND COUPLING MEDIUM DETECTION

(71) Applicant: Signostics Limited, Clovelly Park, South Australia (AU)

(72) Inventor: Andrew John Niemiec, Seaton (AU)

(73) Assignee: ECHONOUS, INC., Redmond, WA (US)

( * ) Notice: Subject to any disclaimer, the term of this patent is extended or adjusted under 35 U.S.C. 154(b) by 220 days.

(21) Appl. No.: 15/485,861

(22) Filed: Apr. 12, 2017

(65) Prior Publication Data

US 2017/0296152 A1    Oct. 19, 2017

(30) Foreign Application Priority Data

Apr. 15, 2016    (AU) ................................ 2016901419

(51) Int. Cl.
| | |
|---|---|
| *A61B 8/00* | (2006.01) |
| *G01N 29/28* | (2006.01) |
| *G01N 29/24* | (2006.01) |
| *G01N 29/11* | (2006.01) |
| *A61B 8/08* | (2006.01) |

(Continued)

(52) U.S. Cl.
CPC .............. *A61B 8/54* (2013.01); *A61B 8/4272* (2013.01); *A61B 8/5207* (2013.01); *A61B 8/5269* (2013.01); *A61B 8/58* (2013.01); *G01N 29/0654* (2013.01); *G01N 29/11* (2013.01); *G01N 29/221* (2013.01); *G01N 29/2456* (2013.01); *G01N 29/265* (2013.01); *G01N 29/28* (2013.01);

(Continued)

(58) Field of Classification Search
CPC ....... A61B 8/54; A61B 8/5207; A61B 8/4272; A61B 8/5269; A61B 8/58; A61B 8/4461; G01N 29/221; G01N 29/02
See application file for complete search history.

(56) References Cited

U.S. PATENT DOCUMENTS 5,588,435 A * 12/1996 Weng .................. A61B 8/0866
                                                          600/443
8,894,579 B2 * 11/2014 Nishihara .............. A61B 8/483
                                                          600/443

(Continued)

*Primary Examiner* — Angela M Hoffa
(74) *Attorney, Agent, or Firm* — Craig Fieschko; DeWitt LLP

(57) ABSTRACT

A method of determining a status of ultrasound coupling medium for performing an ultrasound scan for providing an ultrasound image including plural scanlines ($N_j$) is disclosed. In an embodiment, the method includes operating an ultrasound device to capture an image frame including plural scanlines ($N_j$), each scanline having an associated sample set (s) of intensity values; processing a subset of the associated sample set (s) of values for each scanline to determine a first summation for each scanline; processing plural sets of corresponding intensity values from each of plural scanlines located within a range of a respective scanline to determine a set of difference values for each respective scanline; processing each set of difference values to determine a second summation for each scanline; and generating a status for the ultrasound coupling medium according to a relationship between each of the first summations and each of the associated second summations.

15 Claims, 11 Drawing Sheets

(51) Int. Cl.
*G01N 29/22* (2006.01)
*G01N 29/06* (2006.01)
*G01N 29/265* (2006.01)
*G01N 29/48* (2006.01)

(52) U.S. Cl.
CPC ............ *G01N 29/48* (2013.01); *A61B 8/4461* (2013.01); *A61B 8/467* (2013.01)

(56) References Cited

U.S. PATENT DOCUMENTS

| | | | | |
|---|---|---|---|---|
| 2009/0326609 | A1* | 12/2009 | Doron | A61B 5/0031 607/60 |
| 2014/0305218 | A1* | 10/2014 | Chang | G01N 29/0654 73/620 |
| 2015/0272546 | A1* | 10/2015 | Cheon | A61B 8/469 600/408 |

* cited by examiner

ULTRASOUND COUPLING MEDIUM DETECTION

TECHNICAL FIELD

The present invention relates to ultrasound imaging involving a coupling medium, such as an ultrasound gel. In a typical application, embodiments of the present invention may be used to indicate whether an ultrasound image is affected by, or at least likely to have been affected by, the absence of a sufficient amount of the coupling medium during an ultrasound imaging procedure.

BACKGROUND

Medical diagnostic ultrasound images are formed by generating a high-frequency sound pulse using a transducer, delivering this pulse into the area of interest in the body, receiving the sound echoes from structures within the body, and using information from the echoes to generate an ultrasound image.

Ultrasound imaging involves a transducer that is placed in contact with a patient's skin. An amount of an acoustic coupling medium, such as a conductive gel, is dispensed on the surface of the transducer and onto the patient's skin. The coupling medium couples the transducer with the skin, to assist with transmission of the ultrasonic waves into the body. Ideally the coupling medium provides an acoustic impedance which is part way between that of the transducer and the human body. One commonly used coupling medium is Parker Labs Aquasonic100 transmission gel.

During an ultrasound imaging procedure, insufficient gel, or even a lack of a consistent and desired thickness of the gel, can lead to a reduction in the quality of images produced by the device, and accordingly in measurement values derived from the image.

If, during an ultrasound imaging procedure, no coupling medium were used and the skin was "dry", then a thin air-gap could, and likely would, exist between the transducer and the skin. In such a case, the resultant large impedance mismatch between the transducer and the air would cause most of the sound energy to be reflected back from the air interface, instead of being transmitted into the medium to be imaged, thus providing a very poor quality and unreliable image. Even in circumstances where a small but insufficient amount of gel was present, whilst an image might be generated, the image quality would again be of poor quality and likely still not permit reliable identification of anatomical features.

In addition to the above, in motor-based ultrasound transducers, "reverberations" may be present due to reflections between the transducer elements and an internal coupling medium (such as an oil). Normally these reverberations only affect very shallow regions. However, they may become prominent in regions with insufficient gel for the same lack-of-coupling reasons described above.

It would be desirable to provide a system and method for indicating, during an ultrasound imaging procedure, whether sufficient gel is present before or during imaging, to determine whether an ultrasound image can be considered reliable, or whether additional gel is required.

SUMMARY

Aspects of the inventions disclosed herein include a system and method in accordance with an embodiment of the invention for determining whether sufficient coupling medium is present before or during capture of a desired ultrasound image, determining whether a desired ultrasound image is sufficiently reliable based on a determined presence or lack of sufficient coupling medium, determining whether a depth of image being captured is acceptable or not, or corresponds or likely corresponds to the presence or absence of an air gap, and/or providing one or more forms of feedback to a user to indicate whether sufficient coupling medium has been detected, whether the addition of further coupling medium is recommended or required, whether an absence of sufficient coupling medium is suspected or is to be verified, information related to the depth of image being captured and/or whether an ultrasound session is or is not recommended to proceed or continue based, for example, on the detected or determined or suspected presence or absence of sufficient coupling medium, or on the depth of image being detected. Feedback to the user may take the form of audible and/or visual indications or alarms, and/or control features that interfere with or cease the user's ability to continue to capture ultrasound images without first addressing a detected or determined or suspected absence of sufficient coupling medium to increase the likelihood of the ultrasound images being captured being sufficiently reliable.

For example, according to a first aspect of the disclosure, there is provided a method of determining a status of ultrasound coupling medium for performing an ultrasound scan, the ultrasound scan for providing an ultrasound image including plural scanlines, the method including:

operating an ultrasound device to capture an image frame including plural scanlines, each scanline having an associated set of intensity values;

processing a subset of the associated set of values for each scanline to determine a first summation for each scanline;

processing plural sets of corresponding intensity values from each of plural scanlines located within a range of a respective scanline to determine a set of difference values for each respective scanline;

processing each set of difference values to determine a second summation for each scanline; and generating a status for the ultrasound coupling medium according to a relationship between each of the first summations and each of the associated second summations.

In embodiments, the status indicates whether an image has been, or is at least likely to have been, affected by the presence or lack of sufficient coupling medium.

In an embodiment, processing a subset of values includes processing a subset of values associated with a shallow depth of an image frame of the ultrasound image. In this respect, throughout this specification, references to the terms "shallow depth" are to be understood to denote a reference to a region of the image frame in which reverberations caused by insufficient gel are most likely to be present in the event that the ultrasound coupling medium (that is, the gel) is not present or is present in an insufficient amount. In this respect, in relation to a motor based ultrasound system, the nature of a motor based system is such that reverberations from insufficient gel are typically strongest at shallow regions and reduce with depth. It will be understood that the actual depth range depends on the characteristics of the system, for example, operating frequency, spacing between transducer elements and a lens, lens thickness and the like.

In some embodiments, a shallow depth range is selected which, for a given system, is most likely to include a concentration of reverberations due to gel presence/absence, and which would also include a speckle pattern from tissue when there is sufficient gel. For some embodiments, a "shallow depth" range of between about 0.5 to 1.0 cm from the start of the ultrasound image is selected. In this respect the terms "start of the ultrasound image" denotes a reference to a first (that is, the initial) sample in the set of intensity values for each scanline.

In some embodiments, processing plural sets of corresponding intensity values from each of the plural scanlines located within a range of a respective scanline to determine a set of difference values for each respective scanline involves the processing plural sets of corresponding intensity values over a second depth (herein referred to as a "speckle detect depth"). In some embodiments, the speckle depth may overlap with and extend beyond the shallow depth. However, care needs to be taken to ensure that that the "speckle detect depth" does not extend into a region (such as a large bladder) in which speckle is not present to avoid falsely indicating region as having insufficient gel.

In some embodiments, a region extending from the start of the ultrasound image to the start of the shallow depth is excluded from the determination of the first and second summations as very shallow regions may inherently include an amount of reverberation all the time regardless of whether gel is present or not. For example, in some embodiments, a region extending from 0 mm to 0.5 cm is excluded. Nevertheless, a method which uses the very start of the image may still be made to produce an acceptable result.

In an embodiment, processing a subset of values includes:

for each scanline l, summing intensity values between a first sample number and a second sample number;

generating a vector including each of the summed intensity values; and applying a low pass filter to the generated vector to form a vector of first summations, wherein each of the first summations is associated with a respective scanline.

Each of the plural sets of corresponding intensity values preferably includes a set of difference values of a respective sample number for a set of scanlines located within a predefined range of the respective scanline.

In one embodiment, the set of difference values includes a set of variance values, wherein each variance value in a set of variance values is calculated for a respective one of the plural sets. In such an embodiment the second summation value for a scanline may be determined as the sum of the set of variance values for the scanline.

In another embodiment, the set of difference values includes a set of standard deviation values, wherein each standard deviation value in a set of standard deviation values is calculated for a respective one of the plural sets. In such an embodiment the second summation value for a scanline may be determined as the sum of the set of standard deviation values for the scanline.

The relationship between each of the first summations and each of the associated second summations for a respective scanline may be expressed as a ratio. For example, in some embodiments ratio is expressed as the ratio of the first summation to the second summation.

Preferably, a status is generated as an insufficient ultrasound coupling medium status when the ratio exceeds a predetermined threshold.

According to a second aspect of the disclosure, there is provided an apparatus of determining a status of ultrasound coupling medium for performing an ultrasound scan, the ultrasound scan for providing an ultrasound image including plural scanlines, the method including:

an ultrasound device for capturing an image frame including plural scanlines, each scanline having an associated set of intensity values;

a memory storing a set of computer program instructions;

one or more processors programmed with the set of computer instructions for execution to cause the one or more processors to:

process a subset of the associated set of values for each scanline to determine a first summation for each scanline;

process plural sets of corresponding intensity values from each of plural scanlines located within a range of a respective scanline to determine a set of difference values for each respective scanline;

process each set of difference values to determine a second summation for each scanline; and generating a status for the ultrasound coupling medium according to a relationship between each of the first summations and each of the associated second summations.

Another aspect of the inventions disclosed herein includes a method of determining a status of ultrasound coupling medium for performing an ultrasound scan, the ultrasound scan for providing an ultrasound image including plural scanlines ($N_l$), the method including:

processing the image to compare, for each scanline, a summation of intensity values associated with a respective scanline over a selected first range of depths of the image with a summation of difference values associated with the respective scanline over a second range of depths, each of the difference values being a value determined from intensity values from plural scanlines located within a width range of the respective scanline at a particular depth within the second range; and generating a status indication for the ultrasound coupling medium according to the comparison.

Another aspect of the inventions disclosed herein includes an apparatus for determining a status of ultrasound coupling medium for performing an ultrasound scan, the ultrasound scan for providing an ultrasound image including plural scanlines, the method including:

an ultrasound device for capturing an image frame including plural scanlines, each scanline having an associated set of intensity values;

a memory storing a set of program instructions;

one or more processors programmed with the set of program instructions for execution to cause the one or more processors to:

process the image to compare, for each scanline, a summation of intensity values associated with a respective scanline over a selected first range of depths of the image with a summation of difference values associated with the respective scanline over a second range of depths, each of the difference values being a value determined from intensity values from plural scanlines located within a width range of the respective scanline at a particular depth within the second range; and generate a status indication for the ultrasound coupling medium according to the comparison A particular advantage of the present invention is that it may reduce the likelihood of poor quality ultrasound images which could result from insufficient conductive gel application by providing an operator with an indication of a status of the conductive gel. In this respect, embodiments of the present invention may involve one or more types of indications. By way of example, an indication may include a visible indication, an audible indication (such as a tone), or a tactile indication (such as a vibration).

Accordingly, another aspect of the present invention disclosed herein provides a method of indicating, to a user, whether a coupling medium is present before or during capture of a desired ultrasound image, the method including:

processing an ultrasound image to determine one or more attributes for plural scanlines of the ultrasound image;

comparing the one or more attributes to a predetermined threshold; and providing an indication to a user according to a comparison of the one or more attributes with the threshold.

In some embodiments, a visible indication includes a graphic indication, image or representation (such as a pattern or shape) overlaid over a region of the ultrasound image having image attributes which are associated or at least likely to be associated with insufficient coupling medium application on a particular section of the scan head. In other embodiments of the invention, a visible indication may include a text message alert overlaid onto the ultrasound image indicating an insufficient coupling medium status; a change in the properties and/or appearance (such as a colour) of a section of the image including attributes which are associated or at least likely to be associated with insufficient coupling medium; enabling a status indicator (such as an optical indicator, such as an LED indicator); or modifying the appearance of the ultrasound image so as to flash or otherwise vary or modulate the intensity or other predetermined characteristics of the ultrasound image over a time period.

Alternatively, the indication may include an audible indication (such as a tone or an audible alert message). For example, in some embodiments, an ultrasound probe includes an audio output device for outputting an audible signal in response to determining an insufficient conductive gel status. Alternatively, an audible message in the form of a computer-generated voice may be output which alerts the operator to the insufficient coupling medium status and which, in some embodiments, provides further information, such information identifying the region of the probe's scan head which has been determined to have, or determined to be at least likely to have, insufficient coupling medium.

In other embodiments, in response to detecting an insufficient conductive gel application status, the system may disable capturing of further ultrasound frames until an insufficient coupling medium application status is resolved or is at least acknowledged by the user.

In some embodiments, in the event that captured images include image frames having an associated insufficient coupling medium status, those image frames are stored with a tag identifying the insufficient coupling medium status.

BRIEF DESCRIPTION OF DRAWINGS

Various embodiments of the present invention will be discussed with reference to the accompanying drawings wherein.

In the following description, like reference characters designate like or corresponding parts throughout the figures.

DESCRIPTION OF EXEMPLARY EMBODIMENTS

Figure 1:
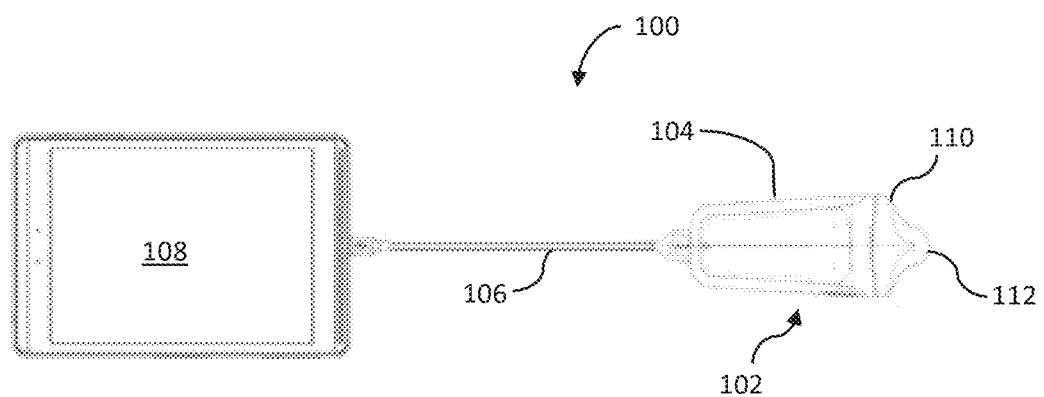
FIG. 1 is a schematic view of an ultrasound system according to an embodiment.

Now referring to FIG. 1, there is shown a view of an ultrasound scan system 100. As shown, the ultrasound scan system includes a processing unit 102, a probe unit 104, and a display 108. These are connected by communications cable 106.

The probe unit 104 includes or is connected to a probe unit scan head 110. The scan head 110 includes a transducer which may be, without limitation, an array transducer having multiple transducer elements, a single element transducer or an array of separate, individual transducers. In the present case, the probe unit 104 is a hand held ultrasonic probe unit.

The processing unit 102 and/or the display unit 108 may be located within the probe unit 104, or located separately. The display unit 108 may include, for example, a touch screen allowing a user to control the functionality of the display unit 108 and the probe unit 104. User controls may be provided on the display unit 108, in the form of touch screen, push buttons and a scroll-wheel. However, it is not essential that such user controls provided.

The scan head 110 includes an acoustic window 112 which contacts the patient during scanning. This acoustic window has an acoustic impedance which is well matched to the acoustic impedance of the body to be imaged. It is desirable to provide the best possible acoustic coupling between the transducer elements and the body to be imaged in order to achieve the best power transfer for acoustic energy into and out of the body.

In use, the probe unit 104 is held against the body of a patient adjacent to the internal part of the body which is to be imaged, with the acoustic window 112 in contact with the patient's skin via a conductive gel coupling. Electronics in the probe unit 104 stimulates the emission of ultrasound energy from each of the one or more transducers. This beam is reflected back to a respective one of the at least one transducer as echoes by the features to be imaged. The at least one transducer in the scan head 110 receives these echoes which are amplified and converted to digital scanline data.

A motor (not shown) moves the at least one transducer such that the ultrasound beam or beams sweep out an area to be imaged. In the present case, electronics for control of the motor are provided in the probe unit 102. It is not essential that embodiments of the invention include a motor as methods according to embodiments are applicable to motor driven and non-motor driven ultrasound probes.

Where a motor is used, the motor may be a linear or a rotary motor. Alternatively, in another embodiment, the linear motor is a linear ultrasonic motor. In this respect, the term "ultrasonic motor" is used throughout this specification. Other terms may be used for devices having the same principle of operation but varying in size, configuration and/or application. These terms include, without limitation, piezomotor, piezoelectric actuator, piezoactuator, and ultrasonic actuator. The term "ultrasonic motor" as used in this specification covers all of these and any other possible terminology which may be used to describe ultrasonically driven moving devices which may be used to perform the invention.

Figure 2:
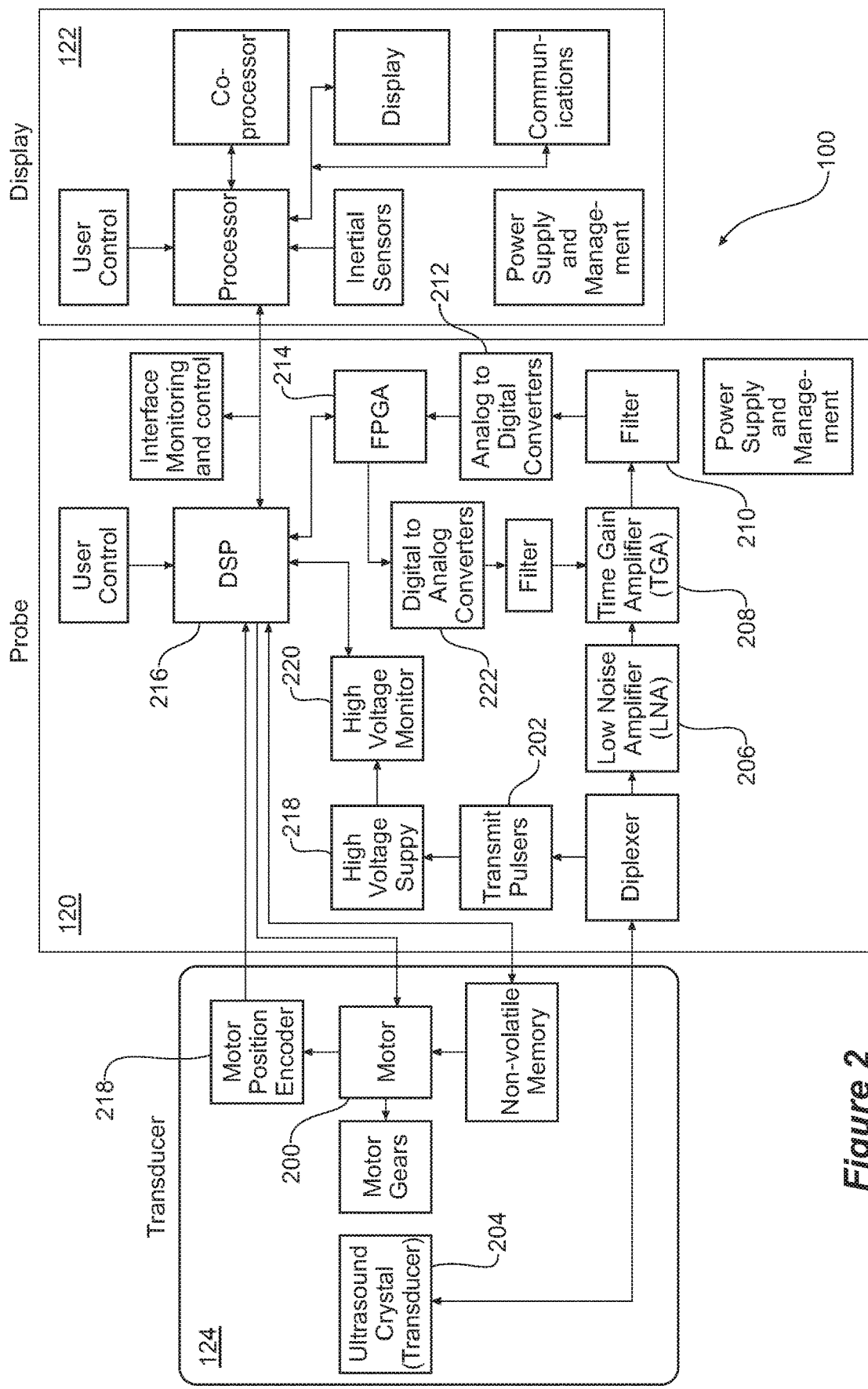
FIG. 2 is a block diagram of an ultrasound system according to an embodiment.

With reference to FIG. 2, there is shown a block diagram of an ultrasound scan system 100 including probe unit electronics 120, display electronics 122 in data communication with the probe unit electronics 120, and the scan head electronics 124. In the present case, the probe unit 104 (ref. FIG. 1) includes the scan head electronics 124 and the probe unit electronics 120 adapted to transmit pulsed ultrasonic signals into a target body and to receive returned echoes from the target body.

In use, the ultrasound scan system 100 (ref. FIG. 1) transmits an ultrasound signal into the target body through the probe unit 102, and receives return signals or "echoes" reflected from the target body. Return signals are received by the probe unit 104 and processed by the processing unit 102 to produce scanlines for generating image frames of an ultrasound image for display on the display 108 as a real-time two dimensional (2D) ultrasound image. The scanlines produced by adjacent ultrasound transducers are separated by a distance f. The transducers transmit and receive ultrasound energy whilst moving or stationary in order to receive a scanline which is a series of echo intensity values returned from features at various depths along a line running into the body to be imaged.

The ultrasound scan system 100 may generate an ultrasound image with respect to a region of interest (ROI) included in the target body, and display the generated ultrasound image with respect to the ROI. In particular, the ultrasound scan system 100 may generate an ultrasound image including a representation of an anatomical feature, such as an organ, within the ROI, thereby enabling a user to ascertain properties of the organ.

Referring again to FIG. 2, the scan head 110 (ref. FIG. 1) shown here includes a transducer arrangement including one or more transducer elements 204 which are controlled to transmit pulsed ultrasonic signals into a medium to be imaged and to receive returned echoes from the medium. In the present case, the transducer arrangement includes eight transducer elements 204 arranged in an annular array, although other arrangements are possible. It is also possible that a different number of transducer elements may be used.

In use, an acoustically conductive gel (hereinafter "the conductive gel") or other coupling medium is applied to the body of a patient adjacent to the internal part of the body which is to be imaged, and the probe unit 102 is brought into contact with the conductive gel and held with the scan head 110 in contact with the patient's skin. Probe electronics 120 located in the probe unit 104 stimulate the emission of an ultrasound beam from the transducer elements of the transducer arrangement. This beam is reflected back to the transducer as echoes from the features to be imaged. The one or more transducer elements of the transducer arrangement receive these echoes which are amplified and converted to digital scanline data. In use, the transducer arrangement may be moved by an operator or by a motor 200 so that it covers all of a selected planar area within the patient's body. The scanline data is then processed and assembled into an image frame for processing.

As shown, the probe unit 102 includes probe unit electronics 120 in communication with transducer arrangement. In the present case, the probe unit electronics 120 includes transmit pulsers 202, low noise amplifiers 206, time gain amplifier 208, filters 210, Analog to Digital converter 212, Digital Signal Processing device 216, Field Programmable Gate Array 214, HV supply 218, HV monitor 220, and Digital to Analog (DAC) converter 222.

Transmit pulser 202 generates a short electrical pulse to create an oscillation in the one or more transducers elements of the transducer arrangement. Each transducer element 204 then generates an ultrasonic pressure pulse which is transmitted into the medium to be imaged. In the present case, eight transducer elements then receive any reflected ultrasonic pressure pulses and convert the received pressure pulse into received electrical signals.

Low noise amplifiers 206 then amplify the received electrical signals for further signal conditioning, which in the present case involves applying time gain amplification (TGA) 208, and filtering the output of the time gain amplifier 208 using a bandpass or low pass filter 210, to provide an analog output signal. The analog output signal is then converted to a digital output via the A/D converter 212. In the present case, digital output values of the A/D converter 212 are input to a field programmable gate array (FPGA) 214 in a low voltage serial format to reduce the number of printed circuit board traces.

The input digital values are de-serialised by the FPGA 214, preferentially delayed, to provide receive focussing, buffered and transferred to the digital signal processing (DSP) device 216 as raw scanline data. The entire process of receiving reflected pulses and transferring the scanline data to the digital signal processing device 216 is defined as acquiring a scanline.

In an embodiment, the digital signal processing device 216 processes each individually acquired scanline by applying a digital filter to the scanline data, detecting the envelope of the scan line data, down-sampling the enveloped data, compressing the raw input data which is preferable 12-bits into a low number of bits, and storing the scanline for scan conversion by a scan converter.

At the completion of a scanline transmit, acquisition, and processing, the FPGA 214 awaits the appropriate time to transmit the next pulse and repeat the process. The timing of the next transmission of a pulse is thus controlled by the FPGA 214. Having acquired a set of scanline acquisitions covering an image area, the acquired scanlines are packaged and transmitted to the display electronics 122 for processing and display as a scan image. In this respect, in embodiments, the digital signal processing (DSP) device 216 provides the below described conductive gel detection functionality of the system 100.

Determining an Insufficient Conductive Gel Status

Figure 3:
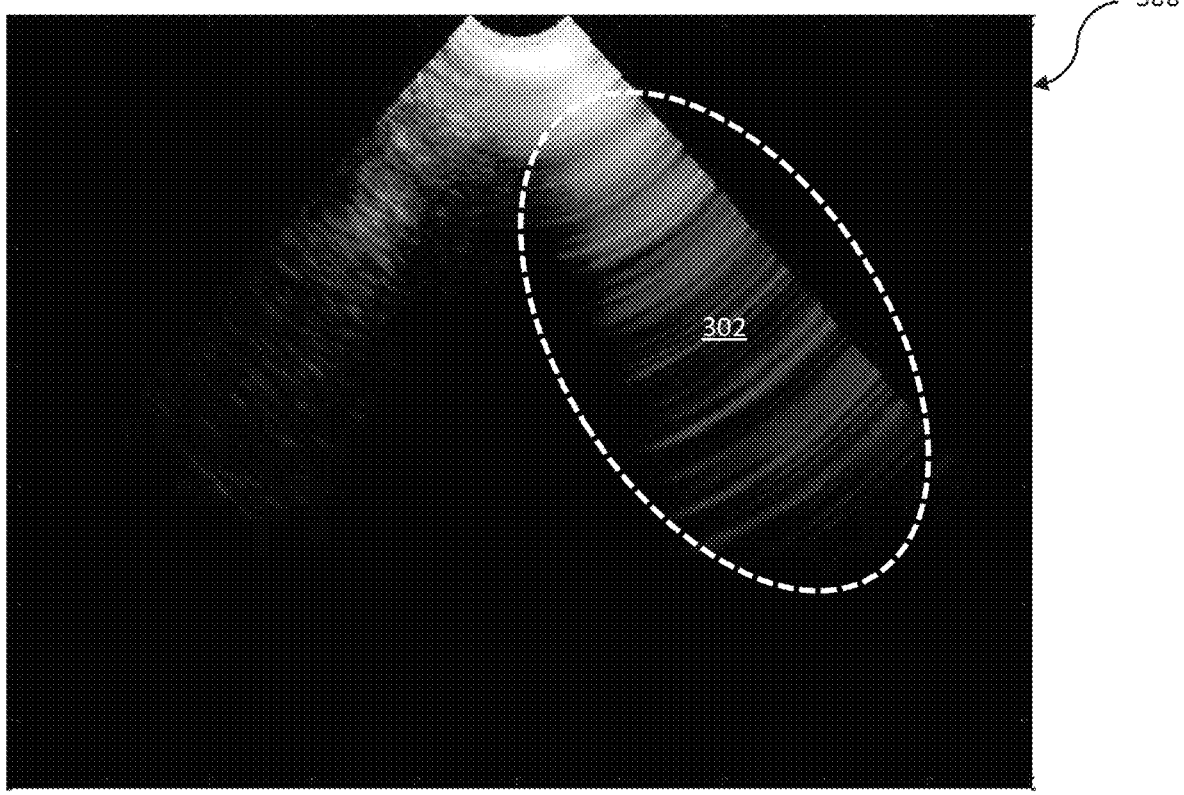
FIG. 3 is an example of a captured image frame including scanlines which have been scan converted.

Turning now to FIG. 3 there is shown an example scan image 300 produced from a set of acquired scanlines which have been "scan converted" to convert the series of individual scanlines into the depicted fan-shaped image by taking into account motor angle.

In this example, part of the scan head 110 has intentionally had insufficient conductive gel applied, and thus the depicted scan image 300 includes a region 302 (highlighted with the dashed line) including the above described "reverberations" resulting from insufficient conductive gel application.

Figure 4:
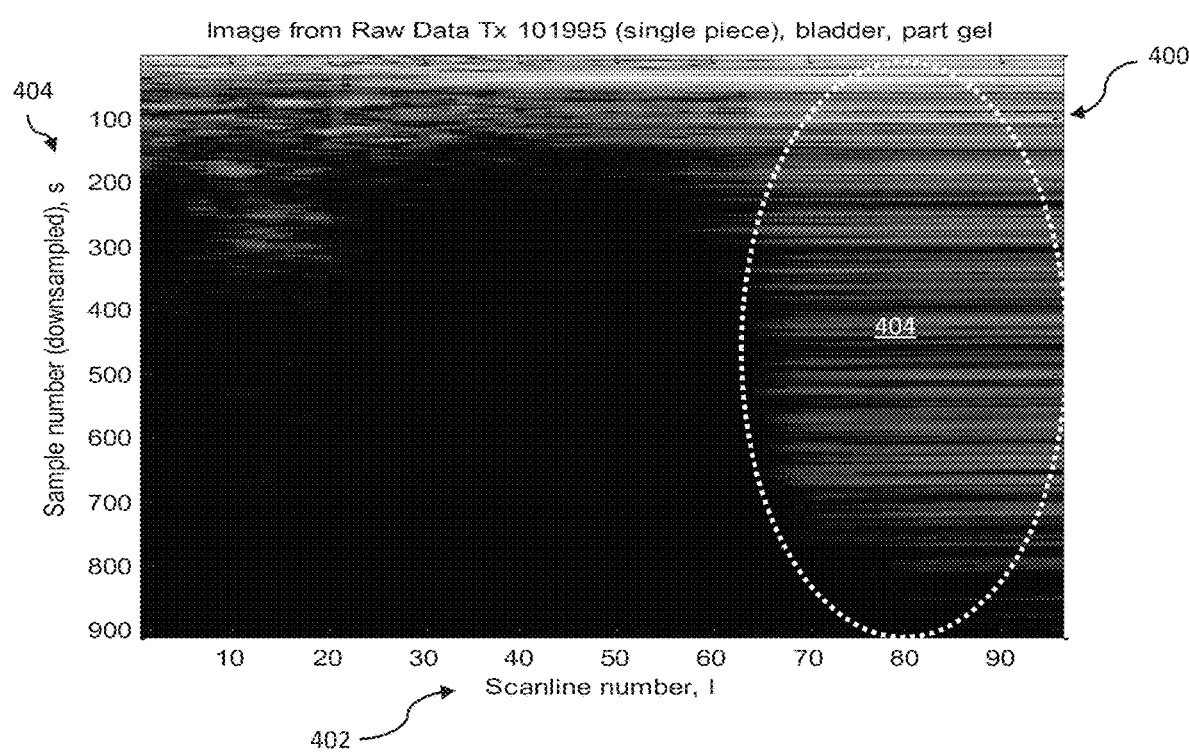
FIG. 4 is an example of a captured image frame including scanlines which have been not been scan converted.

FIG. 4 is a representation 400 of the same scan frame 300 shown in FIG. 3 but without scan conversion. Accordingly, FIG. 4 depicts a "line by line" visualisation which, for the purposes of this specification, is a convenient representation for demonstrating the principles of conductive gel detection.

In this respect, region 404 depicts a region of the image frame having image attributes 3 indicative of insufficient conductive gel.

As shown, the scan frame 400 shown in FIG. 4, includes a number 402, $N_l$ of scanlines, l, (in this case, $N_l$ is 96). Each scanline, l, includes a number $N_s$ of samples s of intensity values 404 (in this case, $N_s$ is 912). It will of course be appreciated that a different number of scanlines and a different number of samples may be used.

Figure 5:
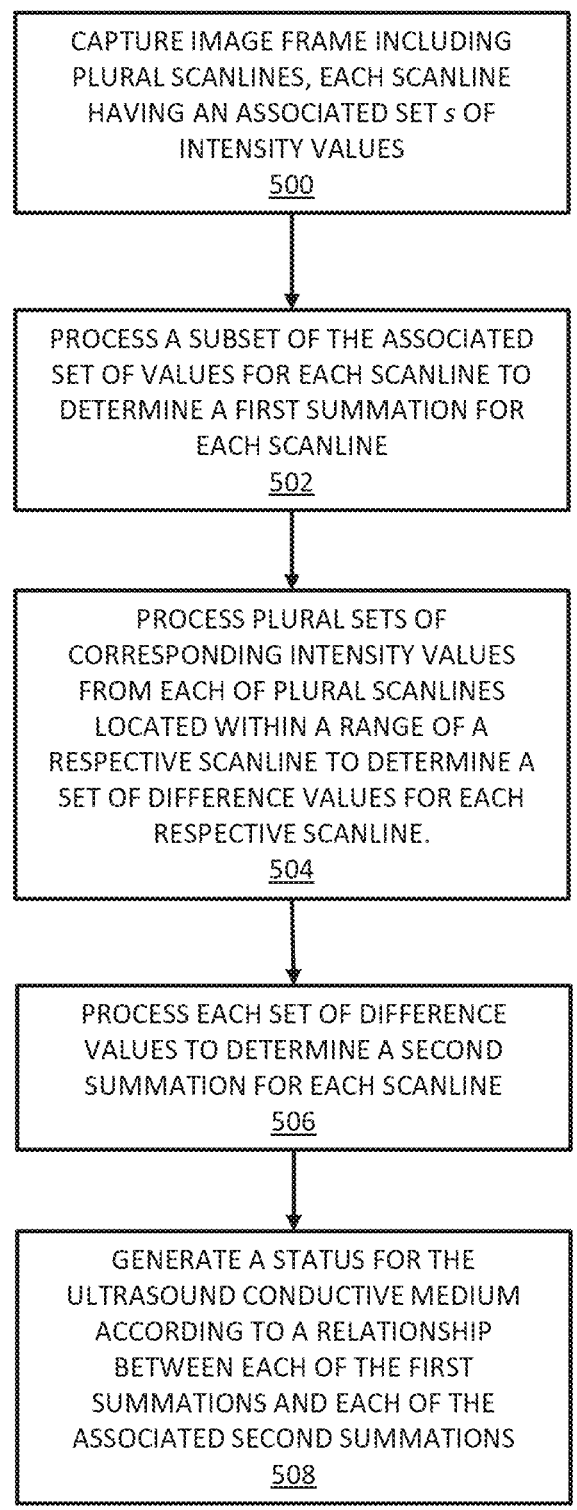
FIG. 5 is a flow diagram of a method according to an embodiment.

Turning now to FIG. 5 there is shown a flow diagram for an embodiment of the present invention determining the status of conductive gel during an ultrasound imaging process. As shown, in general terms the method involves operating 500 an ultrasound device to capture an image frame including plural scanlines, with each scanline having an associated set ($N_l$) of intensity values. Having captured an ultrasound image, as a next step, for each scanline a subset of the associated set of intensity values for each scanline is processed at step 502 to determine a first summation for each scanline.

Figure 6A:
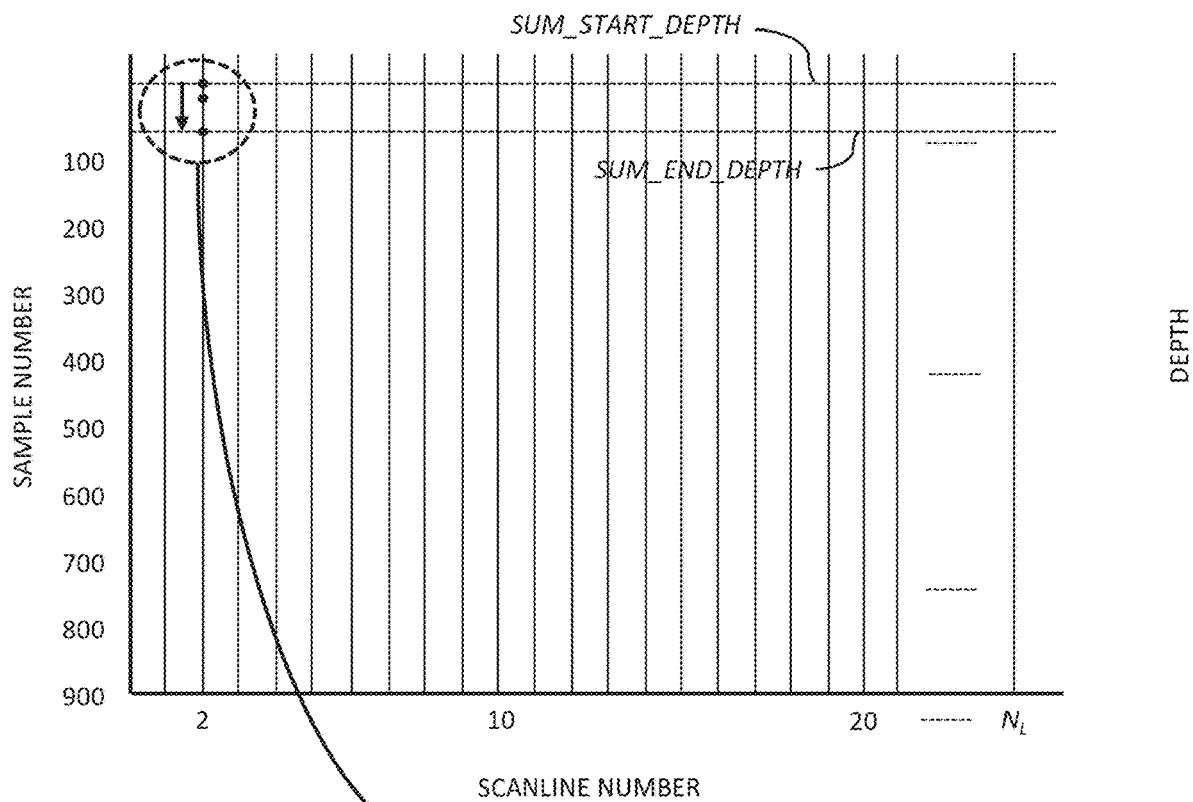
FIG. 6A to 6C is a diagrammatic representation of an approach for determining a first summation for each scanline for use with an embodiment.
Figure 6C:
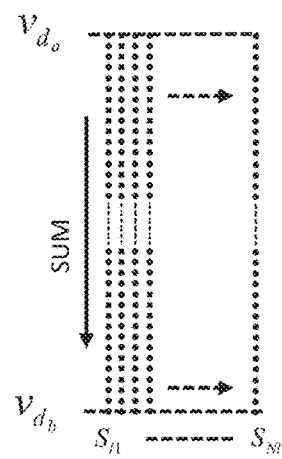
Figure 6B:
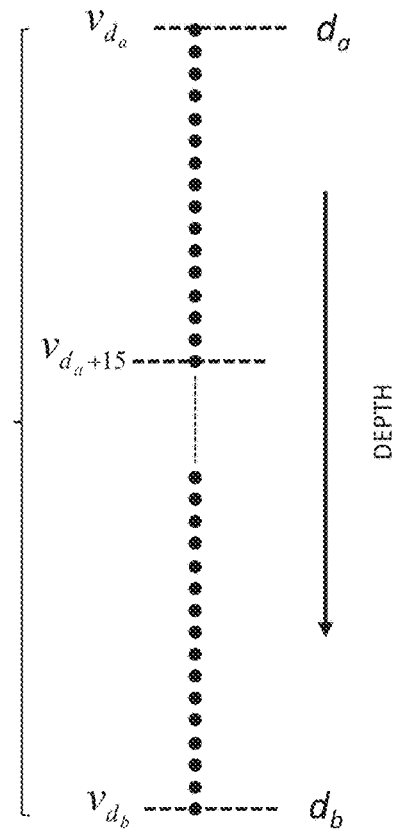
Figure 7:
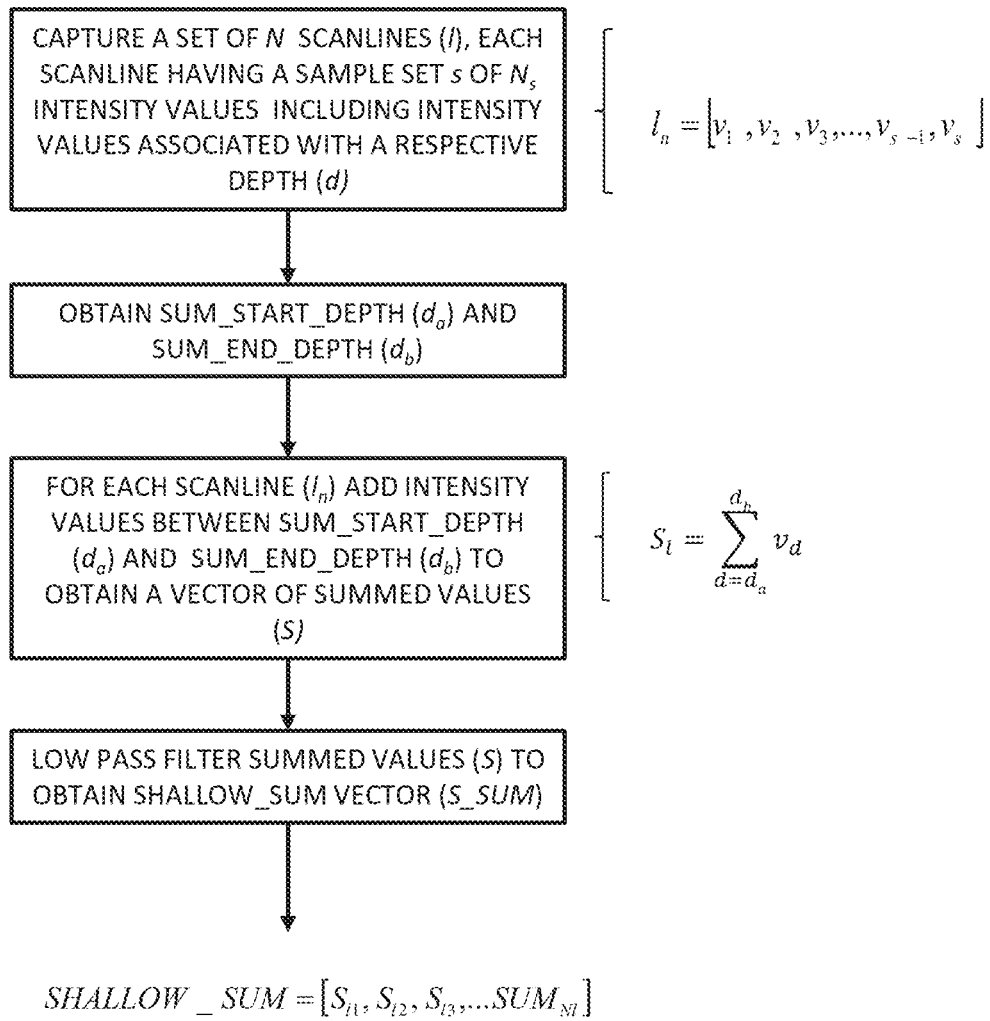
FIG. 7 is a flow diagram of an approach for determining a first summation for each scanline.

In embodiments, and as will be further explained below, the subset of intensity values for determining each first summation corresponds with values located within a defined range of relatively shallow image depths. For example, as shown in FIGS. 6A to 6C, the determination of the first summation for each scanline l may include summing the intensity values in s between a sample number of SUM_START_DEPTH and SUM_END_DEPTH. A vector of length $N_l$ including a set of summed values ($S_l$) for all scanlines may then be constructed. As shown in FIG. 7, in embodiments, a low pass filter is applied to the resulting vector of summed values (S) to provide as an output a vector SHALLOW_SUM of filtered values including the set of first summations. In other words, the vector SHALLOW_SUM includes a first summation for each scanline.

Figure 8:
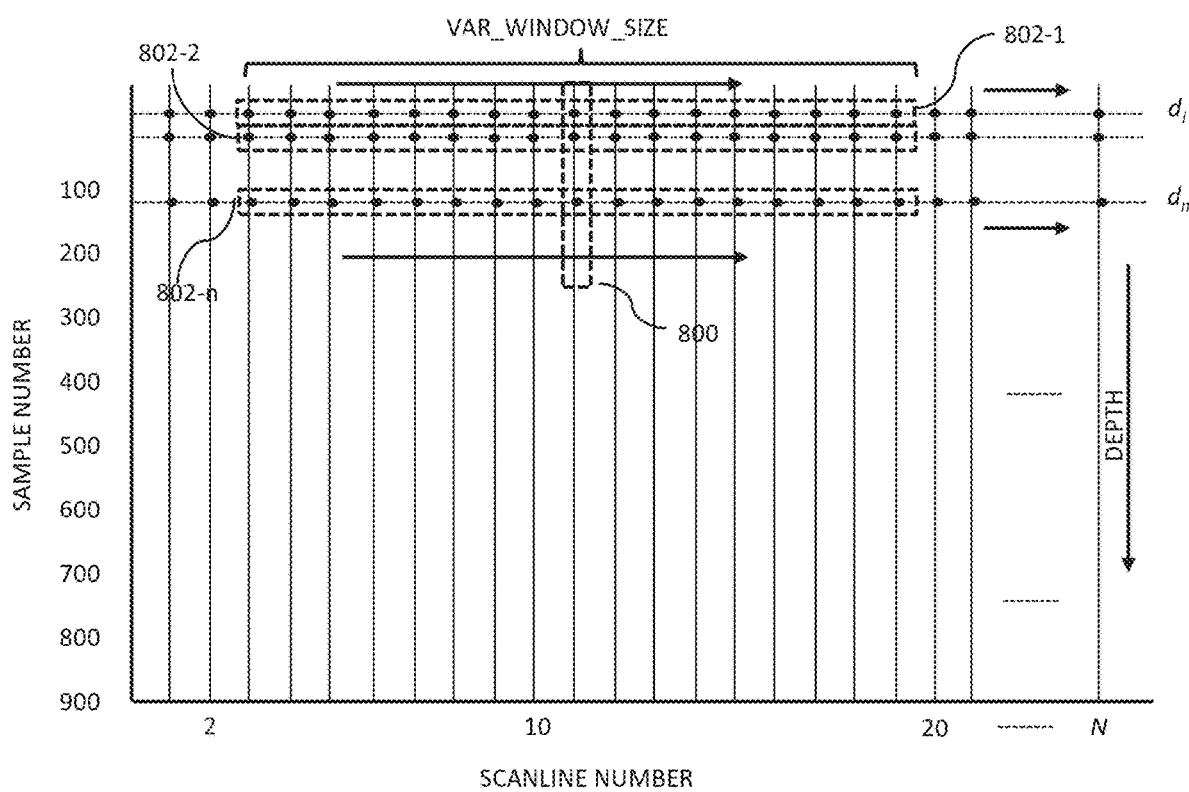
FIG. 8 illustrates an approach for determining a second summation for each scanline for use with an embodiment.
Figure 9:
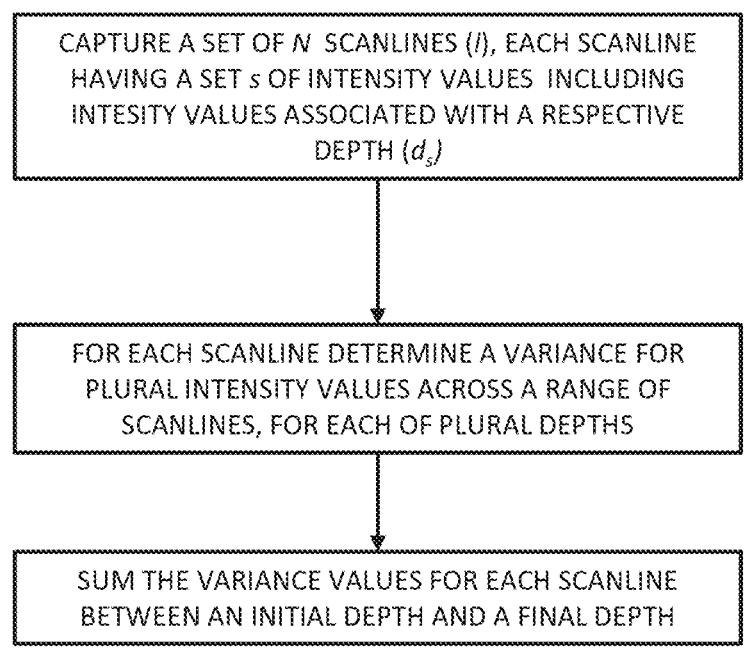
FIG. 9 illustrates an approach for determining a second summation for each scanline.

Referring now to FIG. 8, as a next step, plural sets (802-1, 802-2 ... 802-$n$) of corresponding intensity values from each of the plural scanlines located within a range of a respective scanline 800 are then processed at step 504 to determine a set of difference values for the respective scanline 800. In this respect, the corresponding intensity values are intensity values having the same sample number, and thus are values which are effectively located on a "horizontal line" of constant depth with each being for an associated depth. In some embodiments, low frequency components are removed from each horizontal line of constant depth s by applying a suitable filter. One example of a suitable filter includes a low pass filter in the form of a sliding window box car filter of length 20. Other suitable filters would be within the knowledge of a skilled person. In this respect, it is to be noted that the low pass filter is effectively applied to filter a spatial frequency (in other words, across scanlines).

The resultant values obtained from the application of the low pass filter to each horizontal line of values are then subtracted from the respective original values for the horizontal line, or equivalently a high-pass filter is applied to the line, to produce a set of values as "LF_REMOVED_HORIZONTAL_LINE" in which spatial frequencies below around 2 to 3 cycles per frame are filtered out. An advantage of this approach is that it may remove, or at least reduce, effects of factors that change slightly as a function of scan angle on the variance of the horizontal image lines such as, for example, reverberation lines from a lens that may be glued at a very slight angle, and leave components of higher spatial frequency which are more likely to represent the characteristic 'ultrasound speckle' pattern of tissue. Next, a 'sliding window' moving variance (MOVING_VAR) is calculated across the LF_REMOVED_HORIZONTAL_LINE. In this respect, a window size of 20 to 30 points has been found to be effective for the variance calculation.

For each scanline l, each set of difference values includes a set of variance or standard deviation values, such as, the variance of the predefined windows (ref, FIG. 8, items 802-1, 802-2, 802-$n$) of values centred at l (for example, scanline 800) for an associated constant depth s within a range of depths. In this respect, for each window, the variance may be calculated as:

$$\sigma^2 = \frac{1}{n}\sum_{i=1}^{n}(x_i - \mu)^2$$

Where:
n is the number of sample points the variance is calculated on (that is, the size of the window, VAR_WINDOW_SIZE);
$x_i$=the value of each value of intensity in the variance window;
$\mu$=the mean of all values of intensity in the window $$\left(\mu = \frac{1}{n}\sum_{i=1}^{n}x_i\right)$$

It is also possible that standard deviation could also be used, with suitable changes to detection thresholds. However, it has been found that using variance is computationally more efficient to calculate as no square root is required.

Moving-variance results near the edges of LF_REMOVED_HORIZONTAL_LINE may be obtained using techniques known to those skilled in the art, such as, for example, shortening window size near the edges, extending the output, and/or smoothing. The resultant set of LF_REMOVED_HORIZONTAL_LINE vectors each include a filtered variance value for each scanline at a particular depth.

Each set of difference values is then processed 506 to determine a second summation for each scanline. In the present case, having obtained the vector of values LF_REMOVED_HORIZONTAL_LINE for each horizontal line, respective values from the set of LF_REMOVED_HORIZONTAL_LINE vectors corresponding with a respective scanline (such as scanline 800 in FIG. 8) are summed from a depth of $d_l$=MOVING_VAR_START_DEPTH to a depth of $d_n$=MOVING_VAR_END_DEPTH, to produce a MOVING_VAR_SUM vector having a length of $N_l$ including second summation values for each scanline MOVING_VAR_LINE.

Finally, a status for the ultrasound coupling medium is generated 508 according to a relationship between the each of the first summations (that is, SHALLOW_SUM) and each of the associated second summations (that is, MOVING_VAR_LINE). In the present case, each line, scanline l across the scan image, the relationship is a ratio calculated as:

$$mvar_{ratio} = k * \frac{\text{SHALLOW\_SUM}}{\text{MOVING\_VAR\_LINE}}$$

Where the normalisation constant k is:

$$k = \frac{d_n - d_i}{d_b - d_a}$$

Where:
- $d_i$ is the sample number associated with the MOVING_VAR_START_DEPTH;
- $d_n$ is the sample number associated with the MOVING_VAR_END_DEPTH;
- $d_a$ is the sample number associated with the SUM_START_DEPTH; and
- $d_b$ is the sample number associated with the SUM_END_DEPTH.

It is possible, although not essential, that the same depths are used for both the MOVING_VAR_LINE and SHALLOW_SUM calculations, in which case k=1. An advantage of using k is that it may allow for independent adjustment of START_DEPTH and END_DEPTH parameters while maintaining a fixed value NO_GEL_THRESHOLD. It will be appreciated by a skilled person that omitting k would potentially require a need to recompute NO_GEL_THRESHOLD for any adjustment of either the START_DEPTH or END_DEPTH parameters It is noted that the numerical sample values of these parameters will vary with system and scan settings. However, for sample rate of 20 MHz and envelope downsample rate of 4, suitable values would include:
- MOVING_VAR_START_DEPTH=SUM_START_DEPTH=25 (which corresponds to a depth of approximately 3.8 mm depth)
- MOVING_VAR_END_DEPTH=SUM_END_DEPTH=60 (which corresponds to a depth of approximately 9.2 mm depth)

Finally, for each scanline, l, if MVAR exceeds a predetermined threshold (NO_GEL_THRESHOLD) it is considered that then the scanline has insufficient conductive gel. In this respect, the predetermined threshold (NO_GEL_THRESHOLD) may be a threshold which is set experimentally. In the present case, and a value of 0.6 has been found to be a suitable value for an embodiment.

The value of the NO_GEL_THRESHOLD may be adjusted according to a desired sensitivity. For example, NO_GEL_THRESHOLD may be set to a lower value if a more sensitive detection of lack of gel is desired.

Figure 10:
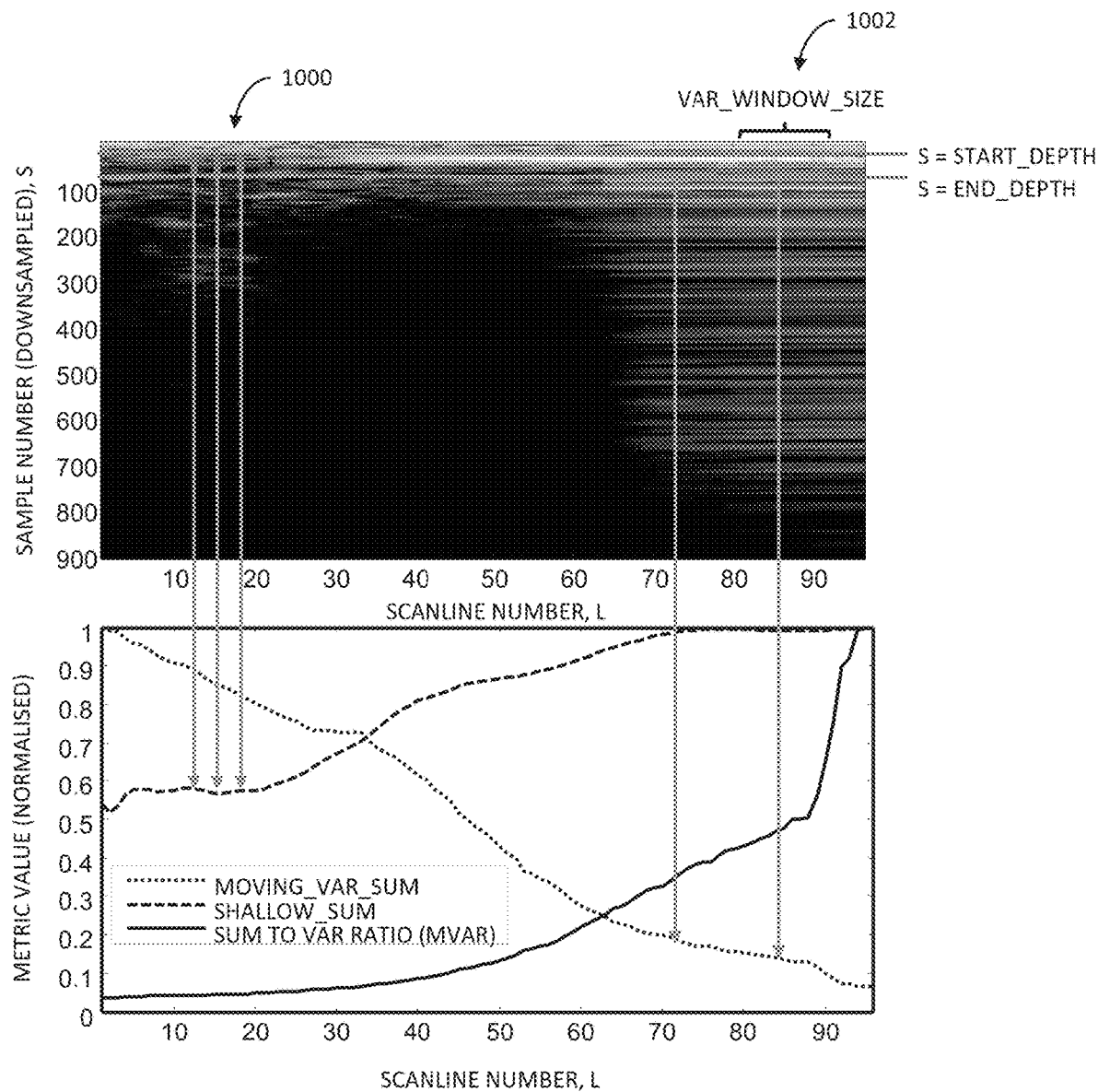
FIGS. 10 and 11 illustrate an example application of a method according to an embodiment.
Figure 11:
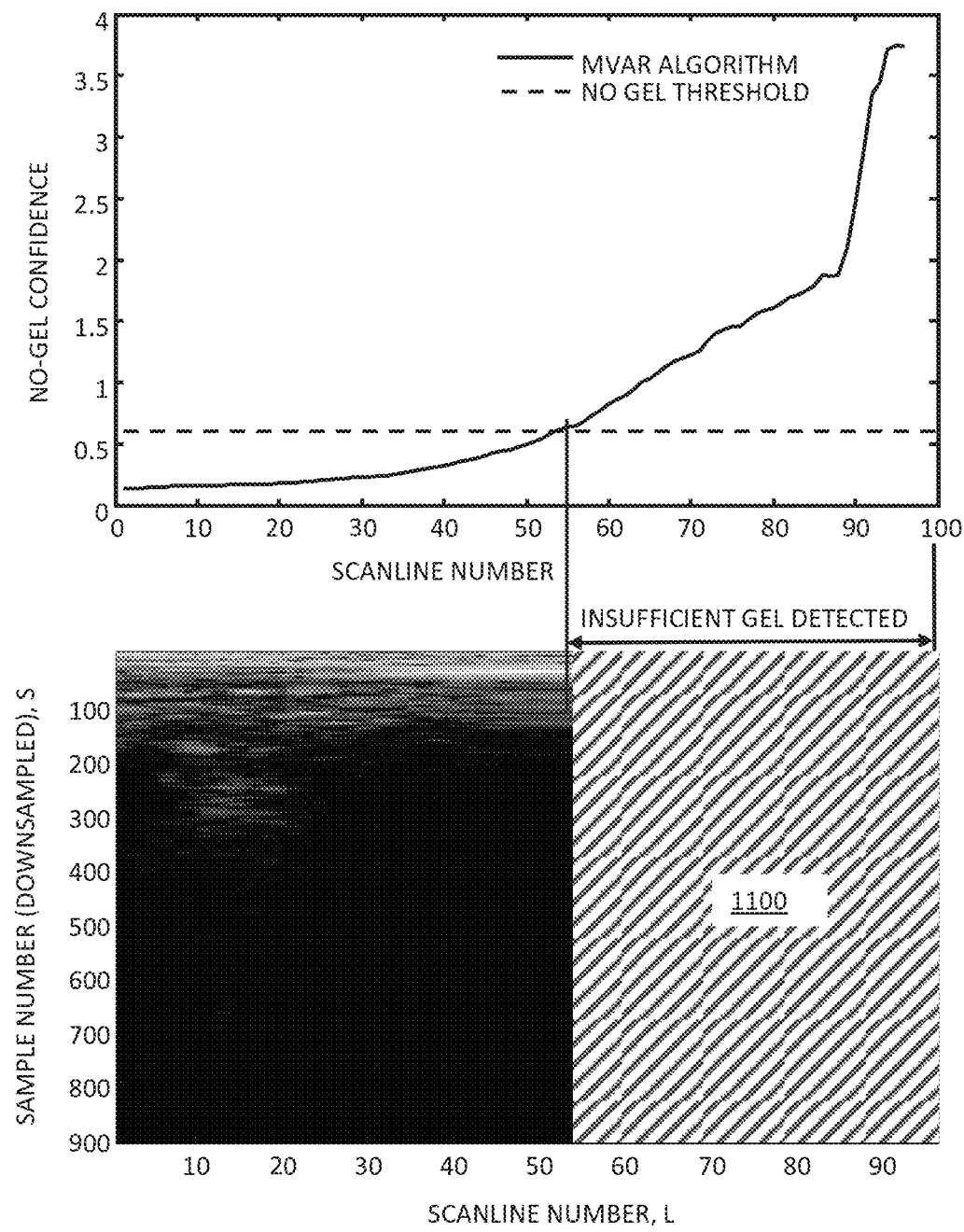

Turning now to FIGS. 10 and 11 there is shown an example application of a method according to an embodiment. FIG. 10 depicts the construction 1000 of a SHALLOW_SUM vector which involves, for each scanline l, determining a summation sum s from START_DEPTH to END_DEPTH and applying a low-pass filter to the summation to generate the SHALLOW_SUM vector including the first summation for each scanline. FIG. 10 also depicts the construction 1002 of the MOVING_VAR_SUM vector by
- Subtracting low frequency components from each horizontal line of constant depth s; and
- For each scanline, l, calculating a variance of the VAR_WINDOW_SIZE 'section' of values centred at L at a constant depth s and summing the variances from a depth S=START_DEPTH to S=END_DEPTH to construct the MOVING_VAR_SUM vector including the second summation for each scanline.

FIG. 10 also depicts the relationship between each of the first summations and each of the second summations which, for each scanline, is calculated as an MVAR using:

MVAR=SHALLOW_SUM/MOVING_VAR_SUM

As shown in FIG. 11, in the illustrated example, a region 1100 where:

MVAR>NO_GEL_THRESHOLD has been identified and would be determined to have a status of insufficient gel. In embodiments, if any of the scanlines are deemed to have, or at least likely to have, insufficient conductive gel, then the user may be prompted to add more gel. Optionally, an indication, a visual indication identifying conductive gel-deficient regions overlaid on the scan image may be provided. In the present case, a graphic (shown as a hashed area) is overlaid over a portion 1100 of the image area indicating that an associated section of the probe head has been determined to have an insufficient conductive gel status and thus that that associated section has, or is at least likely to have, insufficient conductive gel.

A method according to an embodiment, effectively analyses at least two image features which the inventor has found to correspond with insufficient conductive gel, namely, bright shallow regions (represented by the SHALLOW_SUM) are present with insufficient gel, as the lack of conductive gel causes an acoustic impedance mismatch so that most of the energy is reflected back from the transducer lens and causes reverberations rather than penetrating deeper into the body). The less conductive gel there is, the higher the SHALLOW_SUM value will typically be. Secondly, when conductive gel is present, changing body structures across the image frame will cause an increase in variance in signal level when compared to if there were only reverberations present. Thus, higher horizontal line variance (MOVING_VAR_SUM) will be expected when more gel is present.

Either of the above indicators could be used to predict the presence/absence of sufficient gel. However, it has been found that using both of these indicators as a ratio provides for robust prediction of insufficient conductive gel.

Those of skill in the art would understand that information and signals may be represented using any of a variety of technologies and techniques. For example, data, instructions, commands, information, signals, bits, symbols, and chips may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware (including one or more suitable microprocessors), computer firmware or software or instructions, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The steps of a method or algorithm described in connection with the embodiments disclosed herein may be embodied directly in hardware, in a software module executed by a processor, or in a combination of the two. For a hardware implementation, processing may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. Software modules, also known as computer programs, computer codes, or instructions, may contain a number of source code or object code segments or instructions, and may reside in any computer-readable medium such as a RAM memory, flash memory, ROM memory, EPROM memory, registers, hard disk, a removable disk, a CD-ROM, a DVD-ROM, a Blu-ray disc, or any other form of computer-readable medium. In some aspects the computer-readable media may comprise non-transitory computer-readable media (e.g., tangible media). In addition, for other aspects computer-readable media may comprise transitory computer-readable media (e.g., a signal). Combinations of the above should also be included within the scope of computer-readable media. In another aspect, the computer-readable medium may be integral to the processor. The processor and the computer-readable medium may reside in an ASIC or related device. The software codes may be stored in a memory unit and the processor may be configured to execute them. The memory unit may be implemented within the processor or external to the processor, in which case it can be communicatively coupled to the processor via various means as is known in the art.

Further, it should be appreciated that modules and/or other appropriate means for performing the methods and techniques described herein can be downloaded and/or otherwise obtained by computing device. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a computing device can obtain the various methods upon coupling or providing the storage means to the device. Moreover, any other suitable technique for providing the methods and techniques described herein to a device can be utilized.

In one form, the invention may comprise a computer program product for performing the method or operations presented herein. For example, such a computer program product may comprise a computer (or processor) readable medium having instructions stored (and/or encoded) thereon, the instructions being executable by one or more processors to perform the operations described herein. For certain aspects, the computer program product may include packaging material.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like. In embodiments of the present invention, "determining" may include calculating or otherwise deriving a likelihood that a condition exists.

Finally, although the invention described herein is applicable to motor-based ultrasound systems, for non-motor based systems, additionally looking at the brightness in the middle-far field of the image (which will be reduced in non-motor systems as there will not be as many reverberations) may also be used to determine if insufficient conductive gel is applied to non-motor systems where the transducer crystal is applied to the skin directly or through one or more matching layers, but not via a coupling-fluid-filled cavity.

The invention claimed is:

1. A method of determining a status of ultrasound coupling medium for performing an ultrasound scan, the ultrasound scan providing an ultrasound image frame including plural scanlines ($N_l$), the method including the steps of:
    operating an ultrasound device to capture the ultrasound image frame including the plural scanlines ($N_l$), each scanline having an associated sample set (s) of intensity values;
    processing a subset of the associated sample set (s) of values for each scanline to determine a first summation for each scanline;
    processing, for each respective scanline of the plural scanlines ($N_l$), plural sets of corresponding intensity values associated with scanlines located within a predefined range of each respective scanline to determine a set of difference values for each respective scanline;
    processing each set of difference values to determine a second summation for each scanline; and
    determining the status of the ultrasound coupling medium according to a relationship between each of the first summations and each of the associated second summations.

2. The method of claim 1 wherein processing the subset of the associated sample set (s) of intensity values includes processing a subset of values associated with a shallow depth of the ultrasound image frame.

3. The method of claim 1 wherein processing the subset of the associated sample set (s) of intensity values includes:
    for each scanline l, summing intensity values between a first sample number and a second sample number;
    generating a vector including each of the summed intensity values; and
    applying a low pass filter to the generated vector to form a vector of first summations, wherein each of the first summations is associated with a respective scanline.

4. The method of claim 1 wherein each intensity value within each set of intensity values associated with each scanline is associated with a sample number, and wherein each of the plural sets of corresponding intensity values for each respective scanline includes a set of intensity values having a corresponding sample number.

5. The method of claim 4 wherein, for each scanline, the set of difference values includes a set of variance values, wherein each variance value in a set of variance values is calculated for a respective one of the plural sets.

6. The method of claim 5 further including attenuating low frequency components in each distribution of intensity values for a respective depth of the ultrasound image frame to provide the corresponding intensity values for processing to determine a set of difference values for each respective scanline.

7. The method of claim 5 wherein the second summation value for a scanline is determined as the sum of the set of variance values for the scanline.

8. The method of claim 4 wherein, for each scanline, the set of difference values includes a set of standard deviation values, wherein each standard deviation value in a set of standard deviation values is calculated for a respective one of the plural sets.

9. The method of claim 8 wherein the second summation value for a scanline is determined as the sum of the set of standard deviation values for the scanline.

10. The method of claim 1 wherein the relationship between each of the first summations and each of the associated second summations for a respective scanline is expressed as a ratio.

11. The method of claim 10 wherein the ratio is expressed as the ratio of the first summation to the second summation.

12. The method of claim 11 wherein an insufficient ultrasound coupling medium status indication is generated if the ratio exceeds a predetermined threshold.

13. An apparatus for determining a status of ultrasound coupling medium for performing an ultrasound scan, the ultrasound scan providing an ultrasound image frame including plural scanlines, the apparatus including:
an ultrasound device for capturing the ultrasound image frame including the plural scanlines, each scanline having an associated set of intensity values; a memory storing a set of computer program instructions;
one or more processors programmed with the set of program instructions for execution to cause the one or more processors to:
process a subset of the associated set of values for each scanline to determine a first summation for each scanline;
process, for each respective scanline of the plural scanlines, plural sets of corresponding intensity values associated with scanlines located within a predefined range of each respective scanline to determine a set of difference values for each respective scanline;
process each set of difference values to determine a second summation for each scanline; and
generating the status of the ultrasound coupling medium according to a relationship between each of the first summations and each of the associated second summations.

14. A method of determining a status of ultrasound coupling medium for performing an ultrasound scan, the ultrasound scan providing an ultrasound image frame including plural scanlines ($N_j$), the method including the steps of:
processing the ultrasound image frame to compare, for each scanline, a summation of intensity values associated with a respective scanline over a selected first range of depths of the ultrasound image frame with a summation of difference values associated with the respective scanline over a second range of depths, each of the difference values being a value determined from intensity values from a set of the plural scanlines ($N_j$) located within a width range of the respective scanline at a particular depth within the second range; and
determining the status of the ultrasound coupling medium according to the comparison.

15. An apparatus for indicating a status of ultrasound coupling medium for performing an ultrasound scan, the ultrasound scan providing an ultrasound image frame including plural scanlines, the apparatus including:
an ultrasound device for capturing the ultrasound image frame including the plural scanlines, each scanline having an associated set of intensity values;
a memory storing a set of program instructions;
one or more processors programmed with the set of program instructions for execution to cause the one or more processors to:
process the ultrasound image frame to compare, for each scanline, a summation of intensity values associated with a respective scanline over a selected first range of depths of the image with a summation of difference values associated with the respective scanline over a second range of depths, each of the difference values being a value determined from intensity values from scanlines located within a width range of the respective scanline at a particular depth within the second range; and
generating an indication of the status of the ultrasound coupling medium according to the comparison.

* * * * *